US011253276B2

(12) United States Patent
Lefebvre et al.

(10) Patent No.: US 11,253,276 B2
(45) Date of Patent: Feb. 22, 2022

(54) GUIDE FOR POSITIONING AN ORTHOPAEDIC GUIDE PIN ON A BONE STRUCTURE

(71) Applicant: SHOULDER FRIENDS INSTITUTE, Paris (FR)

(72) Inventors: Yves Lefebvre, Strasbourg (FR); Stephane Audebert, Blecourt (FR); Johannes Barth, Meylan (FR); Christophe Charousset, Paris (FR); Jerome Garret, Limonest (FR); David Gallinet, Geneuille (FR); Arnaud Godeneche, Saint Cyr Au Mont D'Or (FR); Jacques Guery, Nevers (FR); Thierry Joudet, Libourne (FR)

(73) Assignee: SHOULDER FRIENDS INSTITUTE, Paris (FR)

( * ) Notice: Subject to any disclaimer, the term of this patent is extended or adjusted under 35 U.S.C. 154(b) by 0 days.

(21) Appl. No.: 17/208,396

(22) Filed: Mar. 22, 2021

(65) Prior Publication Data

US 2021/0204967 A1    Jul. 8, 2021

Related U.S. Application Data

(63) Continuation of application No. PCT/FR2019/052181, filed on Sep. 18, 2019.

(30) Foreign Application Priority Data

Sep. 20, 2018    (FR) ...................................... 18/58525

(51) Int. Cl.
    *A61B 17/17*        (2006.01)

(52) U.S. Cl.
    CPC .............................. *A61B 17/1778* (2016.11)

(58) Field of Classification Search
    CPC combination set(s) only.
    See application file for complete search history.

(56) References Cited

U.S. PATENT DOCUMENTS

| 5,769,856 A | 6/1998 | Dong et al. |
| 2009/0080997 A1* | 3/2009 | Johnson ............. A61B 17/8605 411/347 |

(Continued)

FOREIGN PATENT DOCUMENTS

| FR | 3057454 | 4/2018 |
| WO | 2013060844 | 5/2013 |

(Continued)

OTHER PUBLICATIONS

International Search Report for International Application PCT/FR2019/052181, dated Jan. 28, 2020.

*Primary Examiner* — Samuel S Hanna
(74) *Attorney, Agent, or Firm* — Burris Law, PLLC

(57) ABSTRACT

A guide for positioning an orthopaedic guide pin on a bone structure includes a base having an upper face, a lower face intended to bear against the bone structure, and a through-hole for the pin, said guide including several bearing members able to move in guide holes formed in the base, wherein each bearing member has a lower end facing the lower face and is able to be moved selectively between a retracted position inside the guide hole and at least one deployed position in which the bearing member protrudes from the lower face so as to have a salient lower end intended to bear against the bone structure in order to allow the base to be inclined.

17 Claims, 5 Drawing Sheets

(56) References Cited

U.S. PATENT DOCUMENTS

| | | | | |
|---|---|---|---|---|
| 2009/0118768 A1* | 5/2009 | Sixto, Jr | ............ | A61B 17/8061 |
| | | | | 606/280 |
| 2013/0245631 A1* | 9/2013 | Bettenga | ............ | A61B 17/1746 |
| | | | | 606/91 |
| 2018/0338769 A1* | 11/2018 | Muir | .................. | A61B 17/1684 |

FOREIGN PATENT DOCUMENTS

| WO | 2013060851 | 5/2013 |
|----|------------|--------|
| WO | 2015056097 | 4/2015 |

* cited by examiner

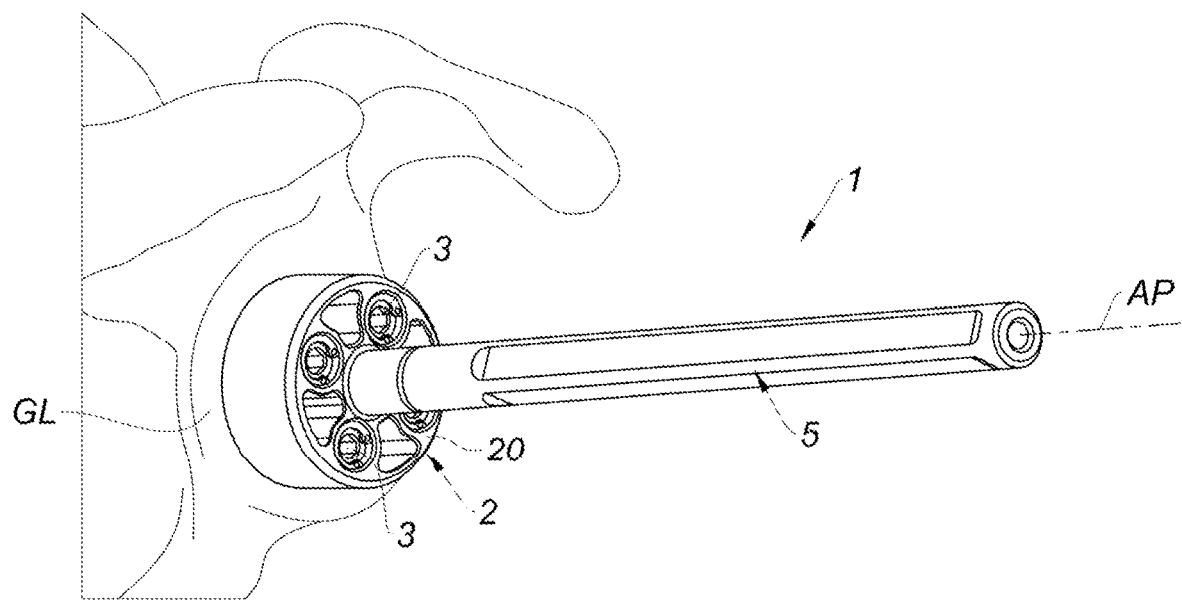
Fig. 1
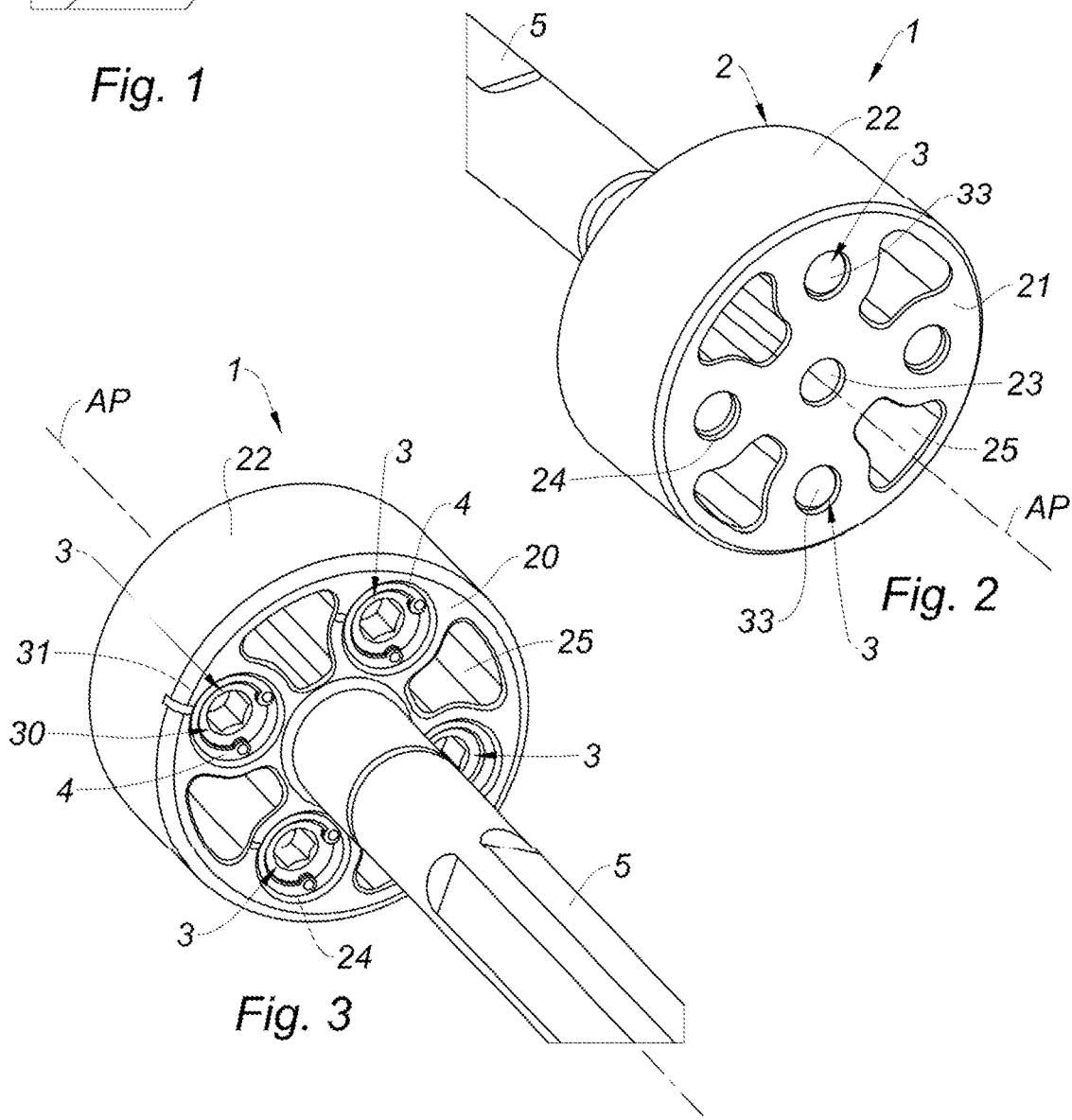
Fig. 2
Fig. 3

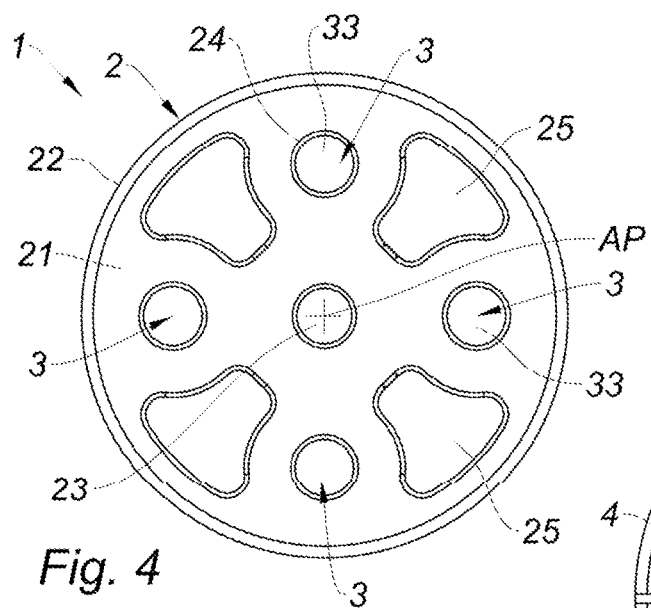
Fig. 4
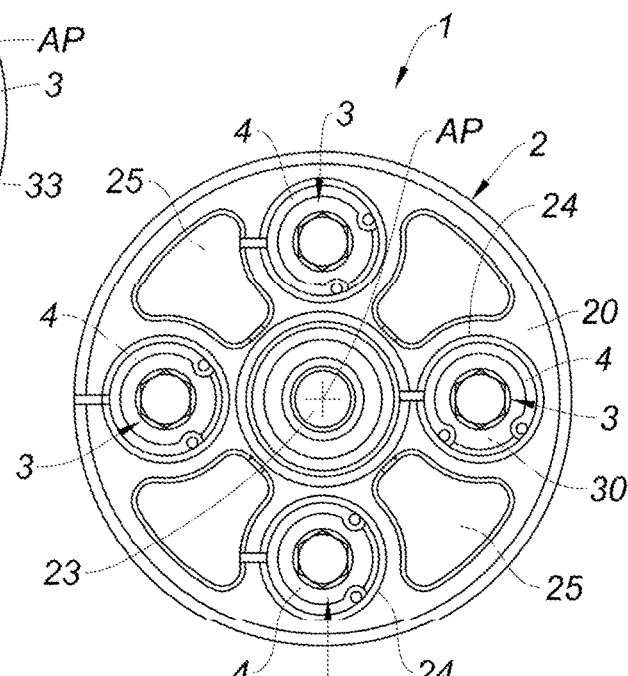
Fig. 5
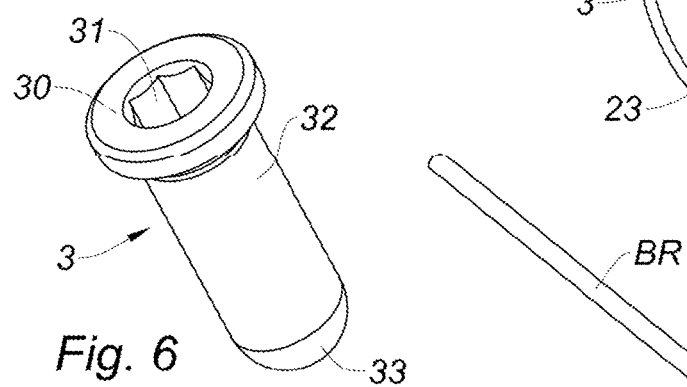
Fig. 6
Fig. 7
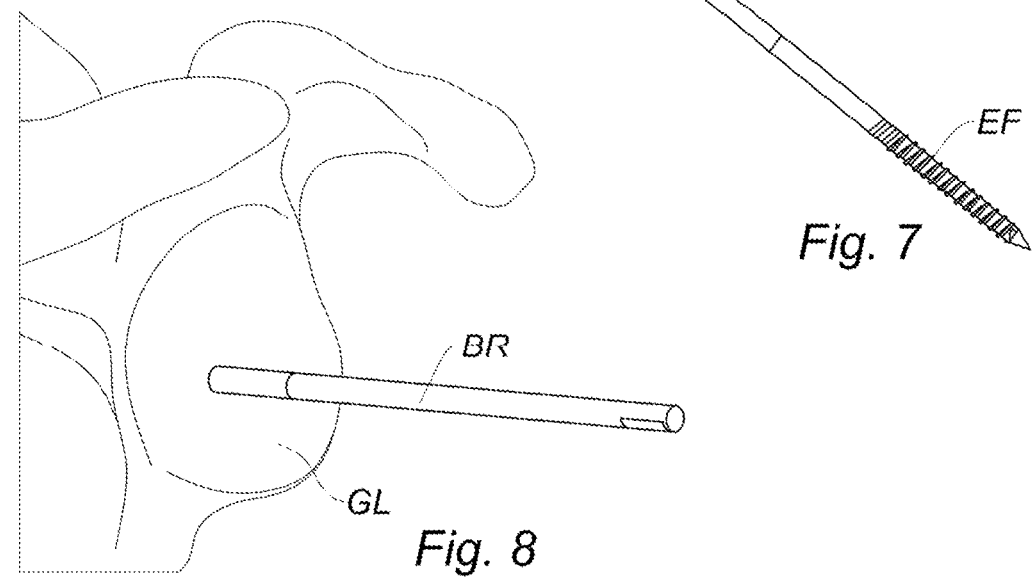
Fig. 8

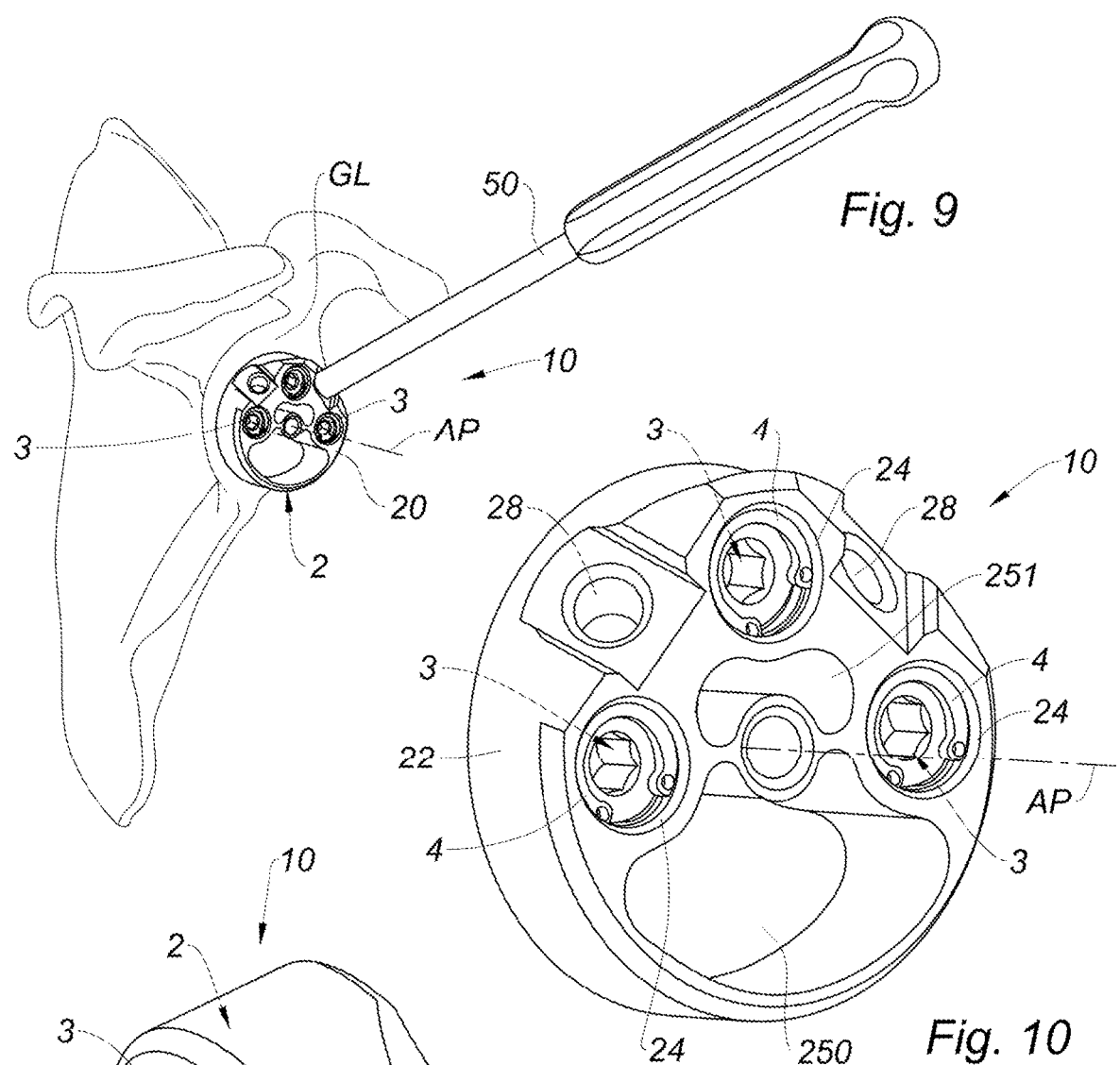
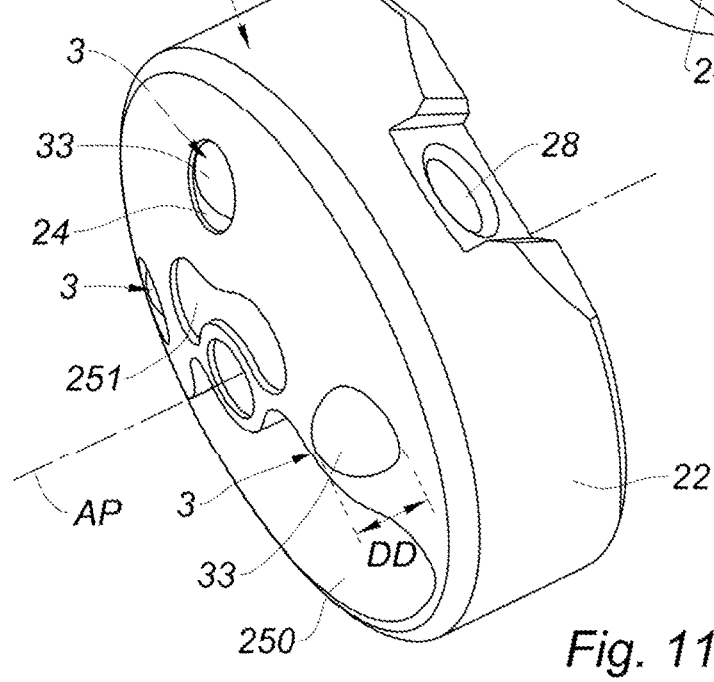
Fig. 9
Fig. 10
Fig. 11

GUIDE FOR POSITIONING AN ORTHOPAEDIC GUIDE PIN ON A BONE STRUCTURE

CROSS-REFERENCE TO RELATED APPLICATIONS

This application is a continuation of International Application No. PCT/FR2019/052181, filed on Sep. 18, 2019, which claims priority to and the benefit of FR 18/58525, filed on Sep. 20, 2018. The disclosures of the above applications are incorporated herein by reference.

FIELD

The present disclosure relates to a positioning guide for positioning an orthopaedic guide pin on a bone structure.

BACKGROUND

The statements in this section merely provide background information related to the present disclosure and may not constitute prior art.

The present disclosure pertains to the field of positioning an orthopaedic guide pin on a bone structure, in particular in preparation for an implantation of an implant on the bone structure, with a particular and non-limiting application in the positioning of an orthopaedic guide pin on a glenoid bone in preparation for an implantation of a glenoid implant of a shoulder prosthesis on the glenoid bone.

When preparing for an implantation of an implant on a bone structure, it is common to resort to an orthopaedic guide pin anchored beforehand into the bone structure so as to serve later on as a guide for one or several preparation tool(s), such as milling tools, cutting tools, digging or drilling tools and compaction tools.

A difficulty for the surgeon is to achieve a desired positioning of the orthopaedic guide pin onto the bone structure, in particular to allow a stable and robust anchorage of the orthopaedic guide pin, while limiting to a minimum damage of the bone structure that should receive anchorages of the implant later on, while bearing in mind that the positioning of the guide pin determines the positioning of the ultimate implant.

In the particular case of a glenoid bone, and in particular of the glenoid cavity of a scapula, this operation of positioning the orthopaedic guide pin on the glenoid bone is complex because of the reduced dimensions of the glenoid bone, so that it is common to resort to a positioning guide which bears on the glenoid bone and which includes a passage orifice intended for passage and for guidance of the orthopaedic guide pin.

Thus, it is known, in particular from the documents EP3057518, EP2770920 and EP2670314, to use a positioning guide specific to a patient, that is to say a single-use positioning guide, manufactured especially to fit to the considered bone structure of a patient, based on pre-surgery image captures and/or on a mold of the bone structure to enable the surgeon to establish the desired orientation for the orthopaedic guide pin and therefore to design the specific positioning guide suited to the patient and adapted to impart the desired orientation.

Although these are advantageous in terms of anatomical fit and therefore in terms of accuracy of the orientation of the orthopaedic guide pin, positioning guides that are specific to a patient are particularly expensive, which may turn out to be prohibitive in some parts of the world, not to mention the desired management and elimination of such specific positioning guides which constitute after surgery wastes that have come into contact with blood, thereby resulting in an additional increase in the costs and in a non-negligible ecological impact.

It is also common to use a non-specific positioning guide, as described in particular in the document FR3057454, which is in the form of a base having a lower face intended to bear at least partially on the glenoid bone and crossed by a passage orifice intended for a passage of the orthopaedic guide pin, with a gripping handle fastened on the base to enable the surgeon to handle and position the base on the glenoid bone. Such a non-specific positioning guide does not allow replicating easily a pre-surgery planning carried out beforehand using common imaging tools such as a scanner, radiography, or MRI imaging. Consequently, this type of non-specific positioning guides calls on the dexterity of the surgeon to provide the set-up of the base on the glenoid bone in order to be able to guide the orthopaedic guide pin according to the desired orientation, with the drawback of a lack of accuracy and ultimately a wrong orientation of the orthopaedic guide pin.

The state of the art may also be illustrated by the teaching of the U.S. Pat. No. 5,769,856, which discloses a drilling guide used to properly position drill bits, wherein this drilling guide comprises a base in which first smooth holes are formed inside which index pins could slide freely and which will cross the base so as to fit into holes drilled in a glenoid bone and which will be used to index the base on the glenoid bone, and second holes used for the passage of the drill bits. However, such a drilling guide is inappropriate for use in the present disclosure, namely for providing the positioning and the orientation of an orthopaedic guide pin that will be used to guide tools for preparing an implantation of an implant on the bone structure.

SUMMARY

This section provides a general summary of the disclosure and is not a comprehensive disclosure of its full scope or all of its features.

The present disclosure provides a non-specific positioning guide intended to be used for different patients, which enables an accurate set-up on the bone structure and therefore an accurate orientation of the orthopaedic guide pin.

To this end, the present disclosure provides a positioning guide for positioning an orthopaedic guide pin on a bone structure, the positioning guide comprising a base having an upper face and an opposite lower face intended to bear at least partially on the bone structure and a passage orifice opening into the upper face and into the lower face and intended for a passage of the orthopaedic guide pin.

The positioning guide comprises at least two bearing members mounted movably within guide holes formed in the base and opening into the lower face of the base. Each bearing member has a lower end directed to the side of the lower face and is selectively movable between a retracted position at least partially inside the corresponding guide hole, and at least one deployed position in which the bearing member protrudes beyond the lower face over a predefined deployment distance in order to have a protruding lower end intended to bear on the bone structure so as to impart an inclination of the base with respect to the bone structure wherein each bearing member, when in a deployed position, is blocked in the direction of a backward movement towards the retracted position.

Thus, based on pre-surgery image captures (for example, scanner images, radiographs, or MRI images) and/or a mold of the bone structure, the surgeon can establish the desired orientation of the orthopaedic guide pin and then deduce the positioning of the positioning guide on the bone structure to impart said desired orientation, which will allow deducing the inclination of the base with respect to the bone structure and therefore the position of each bearing member, either in the retracted position or in the deployed position.

Indeed, when a bearing member is in the deployed position, this bearing member cannot move backward and it will partially peel off the lower face of the base, which will impart an inclination of the base with respect to the bone structure (this inclination depending on the deployment distance and on the location of the bearing member with respect to the bone structure), and which will therefore impart an inclination of the passage orifice so as to coincide the closest with the desired orientation of the orthopaedic guide pin.

The positioning guide may be used for many patients, and it will be adapted to each patient, based on pre-surgery image captures and/or on a mold of the bone structure, by acting on the position of each bearing member.

In the context of the present disclosure, when in a deployed position, each bearing member should be blocked in this deployed position meaning that it cannot move backward (i.e., come back inside the guide hole) when this bearing member bears against the bone structure, of course except when the surgeon acts on this bearing member (in particular by a dedicated tool) to release it and thus make it move backward.

Moreover, the inclination of the base with respect to the bone structure corresponds to an inclination in a three-dimensional space, which covers for example an inclination in a frontal plane (conventionally called "inclination" in surgery) and an inclination in a horizontal plane (conventionally called "anteversion" in surgery). Thus, this inclination may be defined for example by two angles of inclination in two respective reference planes, and in particular by an angle of inclination in a frontal plane and an angle of inclination in a horizontal plane (or anteversion angle).

In one form of the present disclosure, the positioning guide comprises at least three bearing members, and in particular three or four bearing members.

Indeed, with three or four bearing members, the number of bearing points on the bone structure, and therefore the possibilities of inclination of the base with respect to the bone structure and the accuracy of the orientation of the orthopaedic guide pin, are improved.

In one particular form of the present disclosure, each bearing member is selectively movable between the retracted position and several deployed positions associated to distinct deployment distances.

Indeed, with several deployed positions for each bearing member, the possibilities of inclination of the base with respect to the bone structure and therefore the accuracy of the orientation of the orthopaedic guide pin, are also improved.

In another form of the present disclosure, each bearing member is selectively movable by screwing, said bearing member being provided with a tapped rod cooperating with a threaded portion provided in the corresponding guide hole.

Thus, each bearing member is displaced from its retracted position towards a deployed position by screwing, while providing in particular for each screwing turn to correspond to a given step in the deployment distance, for example a step comprised between 0.25 and 1.5 millimeters. Of course, the surgeon may decide to perform, at a given time and for a chosen bearing member, screwing over only one quarter-turn or one half-turn. It should be noted that such a screwing inhibits the backward movement of the bearing members, in the direction of a retraction into the guide holes, when the bearing members bear against the bone structure.

In one variant, each bearing member is selectively movable by sliding, said bearing member being provided with at least one lock cooperating with locking notches provided in the corresponding guide hole, or conversely, said bearing member being provided with locking notches cooperating with at least one lock provided in the corresponding guide hole, each locking notch being associated to a retracted position or to a deployed position.

Thus, each bearing member is displaced from its retracted position towards a deployed position by sliding by pushing thereupon, and by passing from one locking notch to another as it is pushed, while providing in particular for each passage from one locking notch to another to correspond to a given step in the deployment distance, for example a step comprised between 0.25 and 1.5 millimeters.

In one form of the present disclosure, the locking notches are unidirectional, which inhibit the backward movement of the bearing members, in the direction of retraction in the guide holes, when the bearing members bear against the bone structure.

According to one form of the present disclosure, each bearing member, in its retracted position, has a lower end which does not protrude beyond the lower face of the base.

Alternatively, each bearing member may have, when in its retracted position, its lower end protruding slightly beyond the lower face of the base, so that the surgeon can determine the locations and the positions of the bearing members.

According to another form of the present disclosure, each bearing member has an upper end, opposite to the lower end, and each guide hole opens into the upper face of the base so that said upper end is accessible from said upper face side.

Thus, the bearing members are accessible from above to allow displacing them, even when in place on the bone structure.

Alternatively, the bearing members are accessible laterally to allow displacing them.

Alternatively, the bearing members are accessible only from the underside (i.e., from the lower face side) to be able to displace them, which imposes displacing the bearing members beforehand prior to affixing the positioning guide on the bone structure.

In the case of bearing members accessible from above, the upper end of each bearing member may be provided with an imprint, whether male or female, adapted to cooperate with a tool intended to displace the bearing member.

Still in the case of bearing members accessible from above, each bearing member may be blocked in the direction of a come-out from the upper face of the base by a stop disposed inside the corresponding guide hole and located opposite the upper end thereof.

In particular, such a stop may be removably mounted inside the corresponding guide hole.

For example, such a removable stop may include a split ring or a circlip which will be stuck inside the guide hole.

According to one form of the present disclosure, the base has at least one aperture disposed between the guide holes, said aperture being open on the upper face and the lower face.

One or more of such apertures will provide one or several perforations adapted to improve visibility for the surgeon.

According to another form of the present disclosure, the positioning guide further comprises a gripping handle fastened on the base, to enable manual handling thereof by the surgeon.

The gripping handle may be fastened on the passage orifice, and said gripping handle may be tubular and open into the passage orifice so as to enable the passage of the orthopaedic guide pin inside the gripping handle and through the passage orifice.

According to another form of the present disclosure, the gripping handle is remote from the passage orifice.

In accordance with yet another form of the present disclosure, the lower face of the base is planar, convex, or concave.

It may be desired to have a planar or concave (recessed) lower face so that this lower face slightly bears, or not at all, on the bone structure, and thus it is the bearing members that bear on the bone structure, for more accuracy.

The present disclosure also relates to a positioning guide as described hereinabove, for positioning an orthopaedic guide pin on a glenoid bone in preparation for the implantation of a glenoid implant of a shoulder prosthesis on the glenoid bone.

In general, the present disclosure provides a positioning guide for positioning an orthopaedic guide pin on a joint bone structure in preparation for an implantation of an implant of a joint prosthesis on the joint bone structure.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIG. 1 is a schematic perspective view of a first positioning guide according to the present disclosure, in place on a glenoid bone;

FIG. 2 is a schematic perspective bottom view of the first positioning guide of FIG. 1;

FIG. 3 is a schematic perspective top view of the first positioning guide of FIG. 1;

FIG. 4 is a schematic bottom view of the first positioning guide of FIG. 1;

FIG. 5 is a schematic top view of the first positioning guide of FIG. 1;

FIG. 6 is a schematic perspective view of a bearing member alone for the first positioning guide of FIG. 1;

FIG. 7 is a schematic perspective view of an orthopaedic guide pin suited for the first positioning guide of FIG. 1;

FIG. 8 is a schematic perspective view of an orthopaedic guide pin implanted into the glenoid bone of FIG. 1 after positioning by the first positioning guide and after removal of this first positioning guide;

FIG. 9 is a schematic perspective view of a second positioning guide according to the present disclosure, in place on a glenoid bone;

FIG. 10 is a schematic perspective top view of the second positioning guide of FIG. 9;

FIG. 11 is a schematic perspective bottom view of the second positioning guide of FIG. 9;

Figure 14:
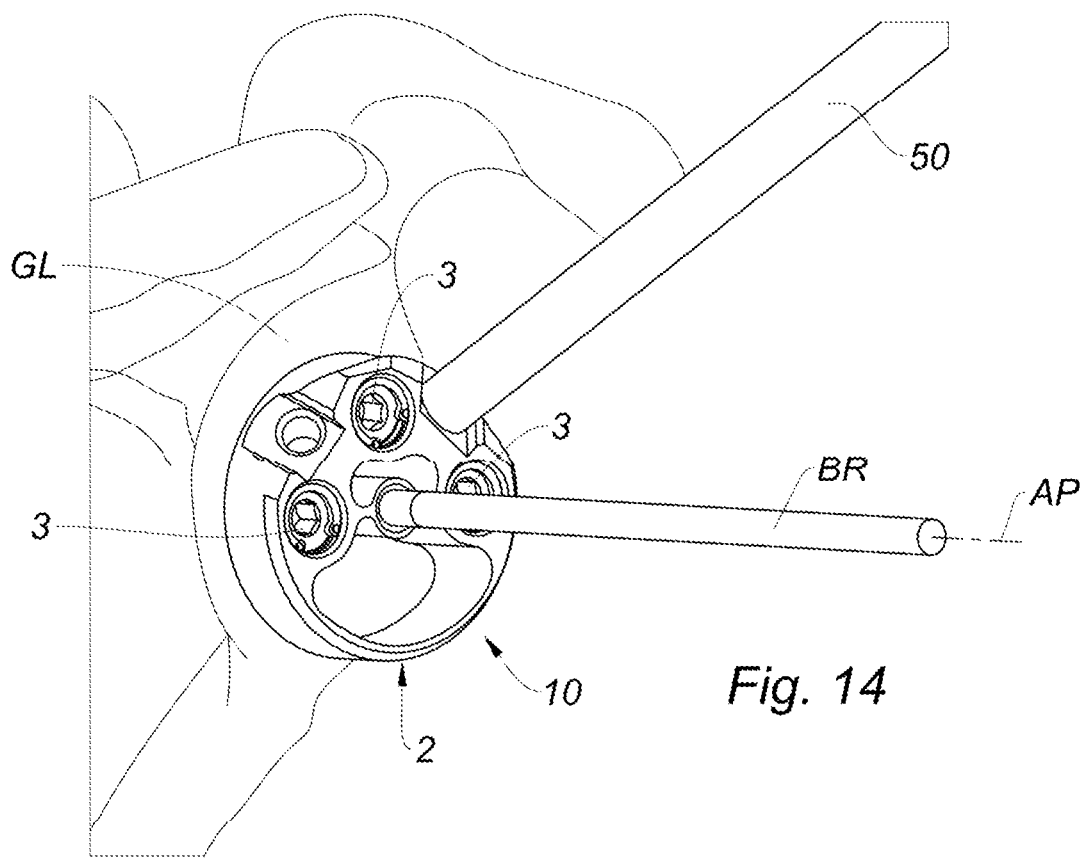
Figure 15:
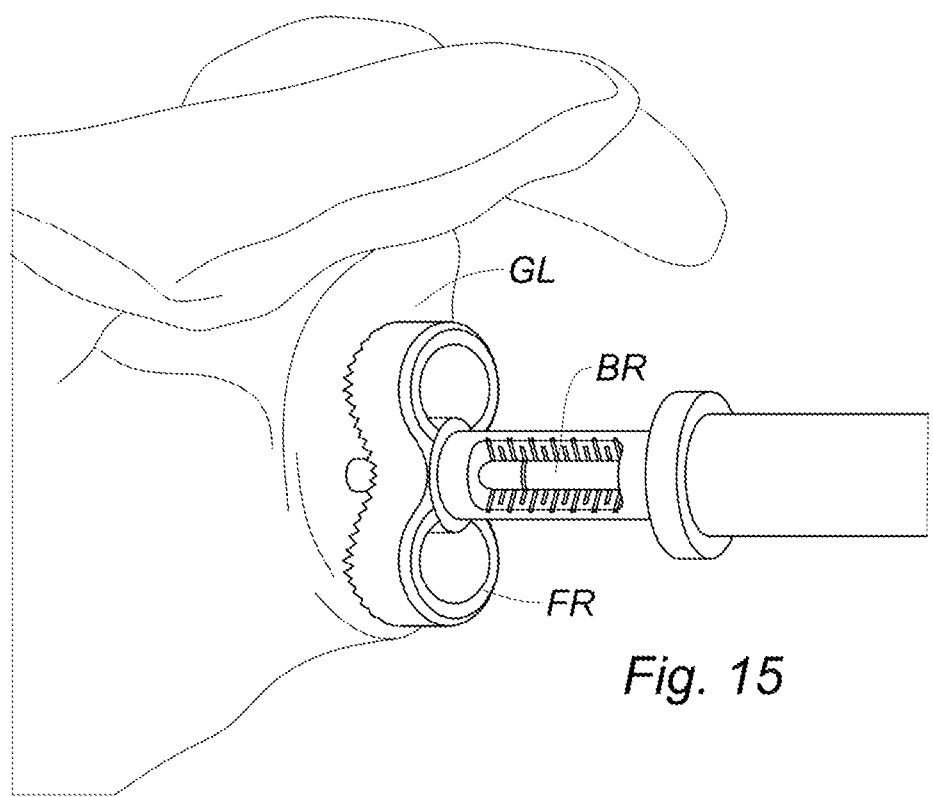

FIG. 14 is a schematic perspective view of the second positioning guide of FIG. 9 in place on the glenoid bone, with an orthopaedic guide pin implanted and oriented into the glenoid bone by the second positioning guide; and FIG. 15 is a schematic perspective view of an orthopaedic guide pin implanted into the glenoid bone after positioning by the first positioning guide or of the second positioning guide, and also of a milling tool which is guided by the orthopaedic guide pin.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

The following detailed description illustrates two forms of a positioning guide 1, 10 according to the present disclosure, namely a first positioning guide 1 illustrated in FIGS. 1 to 5 and a second positioning guide 10 illustrated in FIGS. 9 to 13. In the description of these two examples, and in all figures, identical or similar references refer to identical or similar members, sets of members, functional features or structural features.

In both examples illustrated and described hereinafter, the positioning guide 1, 10 is a positioning guide for positioning an orthopaedic guide pin BR on a bone structure constituted by a glenoid bone GL in preparation for an implantation of a glenoid implant of a shoulder prosthesis on the glenoid bone GL.

The positioning guide 1, 10 comprises a base 2 having two opposite faces, namely:

an upper face 20 opposite to the glenoid bone GL; and a lower face 21 intended to bear at least partially on the glenoid bone GL.

The upper face 20 is substantially planar and orthogonal to the main axis AP described hereinafter. In the first positioning guide 1, the lower face 21 is planar and orthogonal to this main axis AP. In the second positioning guide 10, the lower face 21 is convex (or cambered) while being centered on this main axis AP.

The base 2 also has a peripheral face 22 defining the boundary of the base 2, wherein this peripheral face 22 has a generally cylindrical shape in both illustrated examples.

This base 2 also has a passage orifice 23 passing throughout the base 2 across the thickness thereof and thus opening into the upper face 20 and into the lower face 21. This passage orifice 23 is intended for a passage of the orthopaedic guide pin BR and it extends according to a main axis AP. The passage orifice 23 is in the form of a smooth bore centered on this main axis AP.

This base 2 also has several guide holes 24 passing throughout the base 2 across the thickness thereof and thus opening into the upper face 20 and into the lower face 21. These guide holes 24 extend according to guide axes parallel to the main axis AP.

In the first positioning guide 1, the guide holes 24 are four in number and they are distributed spaced apart by 90 degrees from one another around the main axis AP, with an upper guide hole and a lower guide hole diametrically opposite to one another on either side of the main axis AP and with a right-side posterior guide hole and a left-side posterior guide hole diametrically opposite to one another on either side of the main axis AP.

In the second positioning guide 10, the guide holes 24 are three in number with a right-side posterior guide hole and a left-side posterior guide hole diametrically opposite to one another on either side of the main axis AP and with an upper guide hole at 90° with respect to the two other guide holes 24 around the main axis AP. Thus, in comparison with the first positioning guide 1, the second positioning guide 10 has no lower guide hole.

Figure 12:
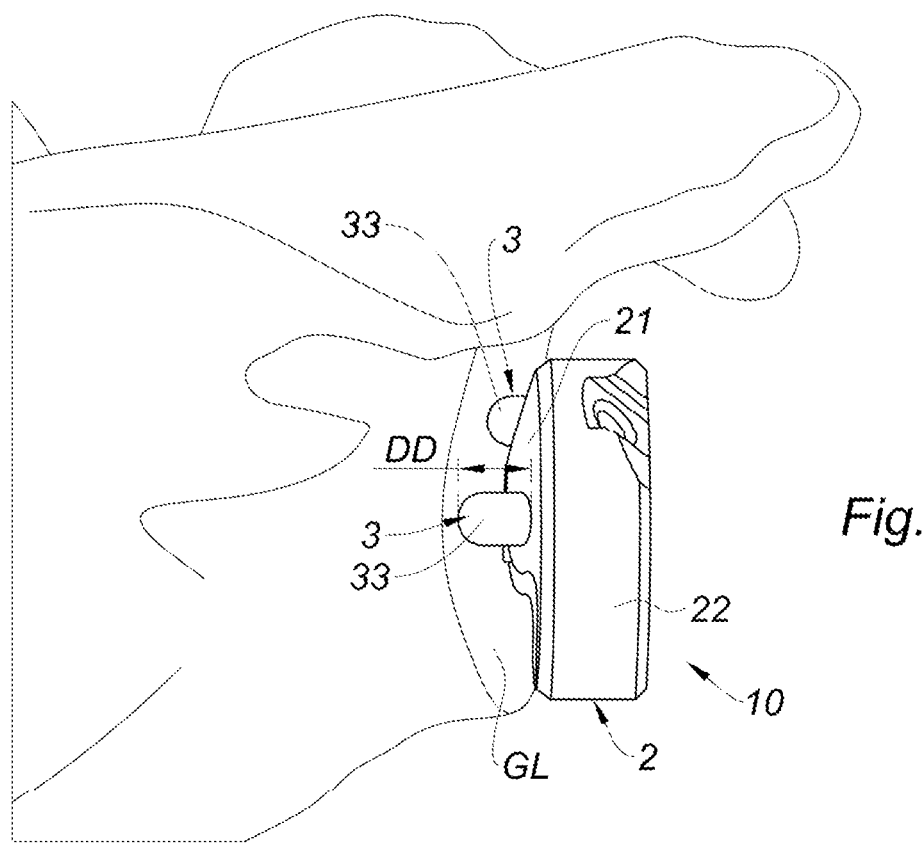
FIG. 12 is a schematic side view of the second positioning guide of FIG. 9 in place on the glenoid bone, visualizing two bearing members in the deployed position and bearing on the glenoid bone.
Figure 13:
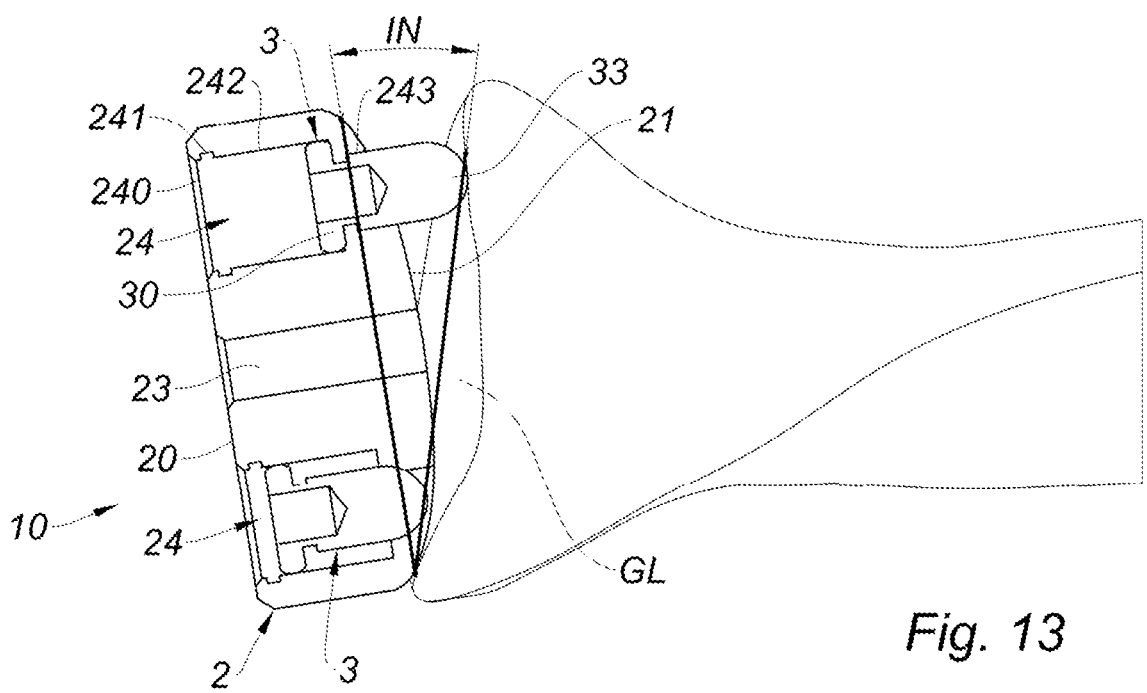
FIG. 13 is a schematic cross-sectional view of the second positioning guide of FIG. 9 in place on the glenoid bone, visualizing a bearing member in the deployed position and another bearing member in the retracted position to impart an inclination of the base with respect to the glenoid bone.

Referring to FIG. 13 regarding the second positioning guide 10, each guide hole 24 successively has, starting from the upper face 20 in the direction of the lower face 21:
a chamfered inlet portion 240;
an annular indentation 241;
a cylindrical and smooth central portion 242; and
a threaded outlet portion 243, i.e. provided with a screwing thread or fillet.

This shaping of the guide holes 24 also applies to the first positioning guide 1.

This base 2 also has apertures 25, 250, 251 passing throughout the base 2 across the thickness thereof and thus opening into the upper face 20 and into the lower face 21. These apertures 25, 250, 251 are disposed between the guide holes 24.

In the first positioning guide 1, the apertures 25 are similar in dimensions and shapes, they are four in number and they are distributed spaced apart by 90 degrees from one another around the main axis AP.

In the second positioning guide 10, the apertures 250, 251 have distinct shapes and dimensions, they are two in number and they comprise a large-sized lower aperture 250 extending between the right-side posterior guide hole and the left-side posterior guide hole and opposite to the upper guide hole, and a small-sized upper aperture 251 extending between the upper guide hole and the passage orifice 23.

For handling of the positioning guide 1, 10, the latter further comprises a gripping handle 5, 50 fastened on the base 2.

In the first positioning guide 1, the gripping handle 5 is fastened on the passage orifice 23, and this gripping handle 5 is tubular according to an axis aligned on the main axis AP, so that this gripping handle 5 opens into the passage orifice 23 so as to enable the passage of the orthopaedic guide pin BR inside the gripping handle 5 and through the passage orifice 23.

In the second positioning guide 10, the gripping handle 50 is remote from the passage orifice 23, and it is provided in particular on the side of the base 2 so as to extend according to an axis inclined with respect to the main axis AP. In particular, this gripping handle 50 may be screwed into a threaded orifice 28 provided to this end in the base 2; two threaded orifices 28 may be provided to the right and to the left depending on whether the glenoid bone GL corresponds to a left or right shoulder.

The positioning guide 1, 10 further comprises several bearing members 3 mounted movably within the respective guide holes 24 of the base 2, and therefore with one bearing member 3 per guide hole 24.

Thus, the first positioning guide 1 comprises four bearing members 3 including an upper bearing member, a lower bearing member, a right-side posterior bearing member, and a left-side posterior bearing member. In turn, the second positioning guide 10 comprises three bearing members 3 including an upper bearing member, a right-side posterior bearing member, and a left-side posterior bearing member.

Referring to FIG. 6, each bearing member 3 is in the form of a screw and comprises:
an upper end 30 forming an enlarged screw head provided with an imprint 31 (for example a female imprint) adapted to cooperate with a tool such as a screwdriver for screwing/unscrewing the bearing member 3; and
a tapped rod 32 extending from the upper end 30 and which terminates in a free end forming a lower end 33, possibly having a cambered or hemispherical shape.

Each bearing member 3 is introduced from above, i.e. from the upper face 20 side, inside a guide hole 24, until the tapped rod 32 starts screwing into the threaded outlet portion 243 of the guide hole 24 and the upper end 30 lies beneath the annular indentation 241.

Afterwards, a removable stop 4, in the form of a split ring or circlip, is removably mounted inside the annular indentation 241 of each guide hole 24, above the upper end 30 of the bearing member 3. Thus, this removable stop 4 is located opposite the upper end 30 of the bearing member 3 and allows blocking the bearing member 3 in the direction of a come-out from the upper face 20 of the base 2. In other words, these removable stops 4 inhibit the bearing members from coming out from above.

The lower end 33 is directed to the side of the lower face 21, whereas the upper end 30 is directed to the side of the upper face 20. Moreover, the upper end 30 is accessible from the side of the upper face 20, so that it is possible to fit a tool into the guide hole 24 from above so as to cooperate with the imprint 31.

Hence, each bearing member 3 is selectively movable by screwing between:
a position fully retracted inside the corresponding guide hole 24, in which its lower end 33 does not protrude beyond the lower face 21 of the base 2 so as not to bear on the glenoid bone GL when in place; and
several deployed positions, wherein in each deployed position, the bearing member 3 protrudes beyond the lower face 21 by a predefined (and non-zero) deployment distance DD in order to have a protruding lower end 33 intended to bear on the glenoid bone GL so as to peel off (or push aside) the lower face 21 of the glenoid bone GL at least partially, which will allow setting an inclination of the base with respect to the glenoid bone GL and therefore setting an orientation of the main axis AP and therefore of the orthopaedic guide pin BR.

This inclination may be defined by at least two angles of inclination in two respective reference planes, such as for example a first angle of inclination in a frontal plane and a second angle of inclination in a horizontal plane (or anteversion angle).

The deployed positions are associated to distinct deployment distances DD, and all it needs is to screw the bearing member 3 to displace it and thus make it switch from its retracted position until reaching the desired deployed position which corresponds to a desired deployment distance DD associated to a desired inclination. By acting on the positions of each of the bearing members 3, the surgeon can thus set the orientation of the main axis AP and therefore of the orthopaedic guide pin BR.

In the example illustrated in FIG. 13, a bearing member 3 (the bottom one) is in the retracted position, whereas another bearing member 3 (the top one) is in the deployed position, and in particular fully deployed, which imparts an inclination of the base 2 with respect to the glenoid bone GL according to a first angle of inclination IN in a frontal plane. Another inclination, in another reference plane, may be provided by acting on the deployment of the other bearing member 3, such as for example according to a second angle of inclination in a horizontal plane (called anteversion angle). In this respect, the base 2 may have a marking on its peripheral face 22 to position the reference planes once in place on the glenoid bone GL, such as for example the marking "UP" shown in FIG. 2.

Once these settings are completed, the surgeon accurately positions the orthopaedic guide pin BR into the glenoid bone GL guided by the passage orifice 23, and the surgeon anchors this orthopaedic guide pin BR into the glenoid bone GL according to the desired orientation. To this end, the orthopaedic guide pin BR has a tapped end EF for anchorage thereof into the bone. Once the orthopaedic guide pin BR is properly anchored and oriented in the glenoid bone GL, the positioning guide 1, 10 is removed, as shown in FIG. 8, and this orthopaedic guide pin BR can serve afterwards as a guide for one or several preparation tool(s), such as a milling tool FR as illustrated in FIG. 15, a cutting tool, a digging or drilling tool or a compaction tool.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A positioning guide for positioning an orthopaedic guide pin on a bone structure, the positioning guide comprising:
   a base having an upper face and an opposite lower face configured to be partially supported on the bone structure, the base also including a passage orifice opening extending into the upper face and into the opposite lower face and configured to receive the orthopaedic guide pin, the base including at least two guide holes opening into the upper face and the lower face of the base; and
   at least two bearing members mounted movably within the at least two guide holes, wherein each of the at least two bearing members has a lower end directed to a side of the lower face and an upper head including an imprint adapted to receive a tool for displacing the at least two bearing members relative to the base, each of the at least two bearing members is selectively movable between a retracted position in which the bearing member is at least partially disposed inside a corresponding guide hole of the at least two guide holes of the base, and at least one deployed position in which the bearing member protrudes past the lower face over a predefined deployment distance such that the lower end is configured to contact the bone structure so as to impart an inclination of the base with respect to the bone structure, wherein the upper head of each of the at least two bearing members, when in the retracted position, is retained within the corresponding one of the at least two guide holes and is inhibited from protruding past the upper face of the base.

2. The positioning guide according to claim 1, wherein the at least two bearing members comprise at least three bearing members.

3. The positioning guide according to claim 1, wherein the at least two bearing members comprise three bearing members.

4. The positioning guide according to claim 1, wherein the at least two bearing members comprise four bearing members.

5. The positioning guide according to claim 1, wherein each of the at least two bearing members is selectively movable between the retracted position and several deployed positions associated to distinct deployment distances.

6. The positioning guide according to claim 5, wherein each of the at least two bearing members is selectively movable by screwing, and is provided with a tapped rod cooperating with a threaded portion provided in the corresponding one of the at least two guide holes.

7. The positioning guide according to claim 1, wherein the lower end of each of the at least two bearing members is inhibited from protruding past the lower face of the base in response to the bearing member being in the retracted position.

8. The positioning guide according to claim 1, wherein the imprint being one of male and female imprint.

9. The positioning guide according to claim 1, wherein each of the at least two bearing members is retained within the corresponding one of the at least two guide holes by a stop disposed inside the corresponding one of the at least two guides holes and located opposite the lower face of the base.

10. The positioning guide according to claim 9, wherein the stop, comprising one of a split ring and a circlip, is removably mounted inside the corresponding guide hole.

11. The positioning guide according to claim 1, wherein the base has at least one aperture disposed between the guide holes, said aperture being open on the upper face and the lower face.

12. The positioning guide according to claim 1, further comprising a gripping handle fastened on the base.

13. The positioning guide according to claim 12, wherein the gripping handle is fastened on the passage orifice opening, and said gripping handle is tubular and opens into the passage orifice opening so as to enable the passage of the orthopaedic guide pin inside the gripping handle and through the passage orifice opening.

14. The positioning guide according to claim 12, wherein the gripping handle is remote from the passage orifice opening.

15. The positioning guide according to claim 1, wherein the lower face of the base is one of planar, convex and concave.

16. The positioning guide according to claim 1, wherein the bone structure is a glenoid bone, and the positioning guide is used in preparation for implantation of a glenoid implant of a shoulder prosthesis on the glenoid bone.

17. The positioning guide according to claim 1, wherein the upper head of each of the at least two bearing members, when in the at least one deployed position, is blocked in a direction of a backward movement towards the retracted position and is inhibited from protruding past the upper face of the base.

* * * * *